United States Patent [19]

Imai et al.

[11] Patent Number: 5,234,971

[45] Date of Patent: Aug. 10, 1993

[54] ODONTOTHERAPEUTICAL MATERIALS

[75] Inventors: Yohji Imai, Chiba; Takahiro Akimoto, Fuji, both of Japan

[73] Assignee: G-C Dental Industrial Corp., Tokyo, Japan

[21] Appl. No.: 796,895

[22] Filed: Nov. 25, 1991

Related U.S. Application Data

[63] Continuation of Ser. No. 631,259, Dec. 20, 1990, abandoned.

[30] Foreign Application Priority Data

Dec. 28, 1989 [JP] Japan ................................ 1-338584
Dec. 28, 1989 [JP] Japan ................................ 1-338585
Oct. 26, 1990 [JP] Japan ................................ 2-287206

[51] Int. Cl.$^5$ ..................... A61K 7/18; A61K 33/16; C08K 3/16
[52] U.S. Cl. ..................... 523/113; 523/116; 424/57; 424/435; 433/212.1; 433/228.1
[58] Field of Search .............. 523/113, 116; 424/57, 424/435; 433/212.1, 228.1

[56] References Cited

U.S. PATENT DOCUMENTS

| 1,183,967 | 5/1916 | Foss | 424/709 |
|---|---|---|---|
| 4,083,955 | 4/1978 | Grabenstetter | 424/606 |
| 4,400,373 | 8/1983 | Hodosh | 424/718 |
| 4,645,662 | 2/1987 | Nakashima | 424/682 |
| 4,677,140 | 6/1987 | Shiotsu | 523/113 |
| 4,684,673 | 8/1987 | Adachi | 523/113 |
| 4,871,786 | 10/1989 | Aasen et al. | 523/113 |

*Primary Examiner*—Paul R. Michl
*Assistant Examiner*—Andrew E. C. Merriam
*Attorney, Agent, or Firm*—Oblon, Spivak, McClelland, Maier & Neustadt

[57] ABSTRACT

An odontotherapeutical material is based on two liquids A and B containing materials capable of forming difficult-to-dissolve precipitations immediately by mixing. The liquids A and B are successively applied on the affected region.

10 Claims, No Drawings

ODONTOTHERAPEUTICAL MATERIALS

This application is a Continuation of application Ser. No. 07/631,259, filed on Dec. 20, 1990, now abandoned.

BACKGROUND OF THE INVENTION

1. Field of the Invention

The present invention relates to lenitives, primers and fillers used for odontotherapies and, more particularly, to lenitives for hypersensitivity, coating primers and root canal filling materials.

2. Prior Art

Among stimuli to teeth are hypersensitivity and pulpalgia that are clincally considered to offer grave problems.

Hypersensitivity is induced, as when vital teeth are put in a senso-sthenic condition by exposure of their dentines and come into physical or chemical contact with cold or sweet-sour foods and drinks, chill, galvanic current, toothbrushes, toothpicks, etc., and causes induced pain and acute pain, although they are transient or fugitive.

The Braöm's hydrodynamic theory about the mechanism of hypersensitivity teaches that an external stimulus applied to the surface of dentine causes a tissue (or pulpal) fluid to move through dentinal tubules in an inward or outward direction and thereby stimulates dentinal nerves in the pulp to cause pain.

As various other theories have also been suggested about the mechanism of hypersensitivity, however, it has so far been treated by such various therapies as set out below.

(1) Mechanical protection of the surface of exposed dental tubules against stimuli of external origin. To this end, a paraformaldehyde-containing "Hyperband" is coated on those surfaces.

(2) Protection of dental tubules against stimuli of external origin by promoting their intra-calcification for their closure. To this end, a "Saforide" containing a diammine silver fluoride solution or an "F vanish" containing a sodium fluoride is coated on the dental tubules —therapy (2-1). Alternatively, the principle of iontophoresis is applied to feed a drug ionized in a solution deeply into the affected region with the aid of current—Therapy (2-2).

(3) A silver nitrate solution is coated on odontoblasts to modify and coagulate them, thereby keeping them from reacting with stimuli of external origin.

(4) Irradiation of laser beams.

These therapies (1)-(4) have been found to be inefficacious for those who suffer from hypersensitivity, i.e. these have the following defects.

For instance, the coating of the paraformaldehyde containing "Hyperband" so as to protect the surfaces of exposed dentinal tubules mechanically against stimuli of external origin—therapy (1)—involves much work, since the powder and liquid components must be mixed and kneaded together for use, and is thus restricted by time, because a period as long as 5-6 hours is needed to set the powder/liquid mixture completely. Moreover, the efficacy of Therapy (1) is generally as low as 50%.

Therapy (2-1), in which the "Saforide" containing a diammine silver fluoride or the F vanish containing a sodium fluoride is applied on dentinal tubules to promote their intra-calcification to close up them and thereby protect them against stimuli of external origin, blackens the affected region coated, and is thus not desirable from the aesthetic point of view and unfit for adults. Moreover, the efficacy of therapy (2-1) is generally as low as 47%. Problems with therapy (2-2) or iontophoresis therapy, in which the principles of electrophoresis is applied to feed a drug ionized in a solution deeply into the affected part with the aid of a current, are that an expensive ion feeder is needed; it involves much work; it causes the patient to feel fright; and the like. Moreover, therapy (2-2) does not pay off for operation, as understood from its efficacy being generally as low as 40%.

Therapy (3), in which odontoblasts are modified and coagulated by the coating of a silver nitrate solution to keep them from reacting with stimuli of external origin, makes the region coated blackish brown, and is thus aesthetically not desirable and unfit for adults. Moreover, it generally shows an efficacy of at most 50%.

Therapy (4) by the irradiation of laser beams, in which laser beams are applied to the dentinal surface of the affected part for about 1 minute, is efficacious, but needs a costly laser irradiator. Moreover, therapy (4) shows an 80% efficacy in some cases, but it is not good in others.

The therapies so far used to treat hypersensitivity do not only involve time-consuming and troublesome work but also may need special equipment. Even without it, they incurs considerable expense. From the patients' point of view, on the other hand, one problem is that the region coated becomes black and so aesthetically not desirable. Another problem is that for lack of durable effect, the affected region has to be coated periodically. Thus, clinicians have yet to find crucially efficacious therapy in spite of many people suffering from hypersensitivity.

Pulpalgia, on the other hand, is induced by physical or chemical factors such as cavity preparation, tooth preparation for fixed prosthodontics, resin filling, traumatic occlusion, changes in atmospheric pressure, fatigue and food debris, and causes every pain from acute, pulsating and lancinating pains to slight pains. Pulpalgia by and large is considered to be causes for similar reasons to those mentioned about hypersensitivity, but is still far from being pathogenically elucidated, as is the case with hypersensitivity.

Accordingly, pulpalgia has so far been treated with liners such as calcium hydroxide preparations, zinc oxide-eugenol cements, glass ionomer cements and carboxylate cements and others. These cements are designed to be mechanically coated on the surfaces of dentinal tubules to protect them against stimuli of external origin.

Problems with the calcium hydroxide preparations are that they are never hardened; they are incapable of forming roentgenograms; they are poor in strength and the like. The zinc oxide-eugenol cements consist of powders and liquid components which have to be mixed and kneaded together for use. Since the liquid/powder ratio should be about 0.5 and a large amount of the powder component should be incorporated into the liquid component, mixing and kneading above all involve much work. Moreover, this cement cannot be used for cases in which a composite resin is to be filled in place, because the liquid component or eugenol interferes with the polymerization of that resin. The zinc oxide-eugenol cements offer problems in strength, etc. as well.

The glass ionomer and carboxylate cements each consist of powders and liquid components which must be mixed and kneaded together for use. Mixing is again troublesome. Because of the liquid having pH of 1.2 to 1.7, the mixture causes a lingering pain to the patient upon filled. Since the cement film is likely to increase in thickness, there is a corresponding decrease in the thickness of a composite resin, offering an aesthetic problem, etc.

The handling problems with the therapies so far used to treat pulpalgia are that mixing and kneading is troublesome; the cement film is likely to increase in thickness and the like. From the patients' point of view, the problems are that they cause a lingering pain to the patients upon filled in place; no aesthetic color matching is achievable and the like.

Thus, clinicians have yet to find crucially efficacious therapy or an efficacious lenitives (or primers) for pulpalgia in spite of many people suffering from pulpalgia.

Various root canal fillers have been used with a view to blocking a passage from the oral cavity to around the root apex by closing up the formed and cleaned root canal and apical foramen, or promoting the growth and calcification of the connective tissue around the root apex. For instance, gutta-percha points, silver points, calcium hydroxide preparations, iodoform preparations, formaldehyde preparations and zinc oxide-eugenol type fillers have been used.

(1) Gutta-Percha Point

This material has suitable plasticity, provides high sealability and is stable, but has difficulty in finding its way through the fine, meandering root canals.

(2) Silver Point

This material is so fine and so rich in elasticity that it is suitable for closing up the meandering root canal, but is so difficult to pull out and so prone to corrode that it can cause tissue disorders.

(3) Calcium Hydroxide Preparation

Problems with this preparation, which is a pasty material designed mainly to promote the healing of ossiferous scars and the formation of hard tissue, are that it is never set; it is lacking in airtightness; it is incapable of being radiographed; it is free from any antiseptic action and the like.

(4) Iodoform Preparation

This material is less harmful to tissue, capable of being radiographed and antiseptic, but has a defect that it is never set upon frilled in place.

(5) Formaldehyde Preparation

This material shows antiseptic and disinfecting actions, but is most likely to put the parodontium of the root apex in ill condition upon when the material is pushed out of it.

(6) Filler Based on Zinc Oxide-Eugenol

This material shows lenitive and antiseptic actions with an increased sealability, but is irritating to the parodontinum of the root tip and prone to contracting.

The following refer to what the lenitives for hypersensitivity is required to process:

(1) it should be unstimulating to the dental pulp and gingival and mitigate or remove any induced pain;
(2) it should cause no damage to teeth;
(3) it should cause no discoloration of teeth;
(4) it should produce its effect through simple work;
(5) it should have an immediate effect;
(6) it should maintain its effect;
(7) it should cause no pain to the patient during or after treatment; and
(8) it should dispense with special hardware or equipment.

The following refer to what the pulpalgia remedy (coating primers) is required to have:

(1) it should be unstimulating to the dental pulp and gingival and mitigate or remove any induced pain;
(2) it should cause no damage to dentin;
(3) it should cause no discoloration of dentin;
(4) it should produce its effect through simple work;
(5) it should have an immediate effect;
(6) it should maintain its effect;
(7) it should cause no pain to the patient during or after treatment;
(8) it should dispense with special hardware or equipment, and
(9) it should not inhibit the polymerization of resin.

Table 1, given below, shows how efficacious the conventional therapies are against hypersensitivity and pulpalgia.

TABLE 1

| Trade Name | (1) | (2) | (3) | (4) | (5) | (6) | (7) | (8) | (9) | Efficiency |
|---|---|---|---|---|---|---|---|---|---|---|
| Hyperband | ○ | ○ | Δ | Δ | x | ○ | ○ | ○ | | 50% |
| Saforide | Δ | Δ | x | Δ | Δ | Δ | Δ | ○ | | 47% |
| Silver Nitrate Solution | Δ | Δ | x | Δ | Δ | Δ | Δ | ○ | | 50% |
| Laser Beams | ○ | ○ | ○ | ○ | ○ | ○ | ○ | x | | 80% |
| Calcium Hydroxide Preparation | ○ | ○ | Δ | ○ | Δ | Δ | ○ | ○ | ○ | 50% |
| Zinc Oxide Eugenol Cement | ○ | ○ | Δ | x | Δ | Δ | ○ | ○ | x | 50% |
| Carboxylate Cement | ○ | ○ | Δ | Δ | ○ | ○ | x | ○ | ○ | 50% |

○: Satisfactory
Δ: Less Satisfactory
x: Unsatisfactory
(1)~(9): See the above

As can be understood from Table 1, the conventional hypersensitivity therapies do not only offer problems that, by way of example alone, they are irritating to the dental pulp and cause discoloration of gingival and dentin, but are also disadvantage in that, by way of example alone, they make mixing and kneading work troublesome and their effect is neither reliable nor durable. Also, the conventional pulpalgia therapies do not only pose problems that, by way of example only, they are irritating to the dental pulp and give rise to discoloration of gingival and dentin, but also are disadvantageous in that, by way of example only, they may make resin filling a taboo.

It is therefore an object of this invention to provide an odontotherapeutical material which can successfully meet both what is required for treating hypersensitivity and what is required for treating pulpalgia.

The following refer to what the root canal filler is required to possess:

(1) it should have a good biocompatibility with a living body;
(2) it should be unstimulating and harmless to part of the parodontinum around the apical foramen;
(3) it should be unporous;
(4) it should cause no discoloration of dentin;
(5) it should undergo no change in its quality;

(6) it should be removed, if necessary;
(7) it should be of radiopacity; and
(8) it should be easy to handle.

Among currently available root canal fillers, there is a sealer capable of sealing up the apical foramen in the root canal, which is essentially required to have a good biocompatibility. To this end a gutta-percha point is now mainly used. Even with a commercially available root canal length gauge, however, it is nearly impossible to accurately measure the size of the root apex in the root canal. A problem with the gutta-percha point is that when actually filled under pressure into the root canal, it thrusts through the root apex, or it is not well sealed up.

According to what the Brännström's hydraulic dynamics theory teaches about why hypersensitivity occurs, an external irritation applied to the surface of dentin causes a tissue (or pulpal) fluid to flow through dentinal tubules and thereby give rise to a variation of their internal pressure, irritating dentinal nerve fibers to cause pain. Thus, a key to solving the problems associated with the conventional hypersensitivity and pulpalgia therapies and meeting what is required for treating them is to control the fluid movement in the dentinal tubules. From the results of various studies made to achieve that, it has now been found that it is desired to seal up dentinal tubules with a material which is difficult to dissolve in water and unstimulating. It has also been noted that such a material is required to seal up elongated dentinal tubules.

SUMMARY OF THE INVENTION

In view of the foregoing, the inventors have made intensive and extensive studies in search of a material which can seal up elongated dentinal tubules and be of greater safety in use, succeeding in finding an odontotherapeutical material according to this invention.

Thus, the present invention provides a two-pack system consisting of liquids A and B designed to be successively applied on the affected part on which they are allowed to react with each other to form a substance difficult to dissolve in water. This substance can then be used to seal up elongated dentinal tubules or the root apex in the root canal.

More specifically, liquid A is mainly an aqueous solution containing 1-70% of one or more of sodium, potassium and lithium salts of an inorganic or organic acids, while liquid B is chiefly an aqueous solution containing 1-70% of one or more of chlorides, nitrates, sulfates and acetates of calcium, zinc, strontium, magnesium, aluminium, barium, iron, copper, silver, lead and tin. For use, liquids A and B are mixed together.

The substances used for liquid A in the form of a 1-70% aqueous solution may be one or more of sodium, potassium and lithium salts of phosphoric acid, pyrophosphoric acid, tripolyphosphoric acid, metaphosphoric acid, polyphosphoric acid, phosphonic acid, phosphinic acid, sulfuric acid, sulfurous acid, carbonic acid, hydrogen fluoride, hydrogen sulfide and silicic acid or members are acidic groups carboxyl, phosphoric, thiophosphoric, pyrophosphoric, phosphonic, phosphinic and sulphonic groups, all being water-soluble. Part of water may be substituted by alcohol, acetone, dimethyl sulfoxide or the like. Specific mention is made of trisodium phosphate, disodium phosphate, monosodium phosphate, sodium pyrophosphate, dihydrogen sodium pyrophosphate, sodium tripolyphosphate, sodium metaphosphate, sodium phosphate, sodium posphite, sodium sulfate, sodium sulfite, sodium carbonate, sodium fluoride, sodium sulfide, sodium silicate, sodium benzoate, sodium salicylate, sodium oxalate, sodium malate, sodium malonate, sodium citrate, sodium succinate, sodium gluconate, sodium acrylate, sodium methacrylate, sodium vinyl benzoate, sodium styrene sulfonate, sodium phthalate and sodium trimellitate as well as polymers or copolymers of sodium acrylate, sodium methacrylate or sodium maleate. Use may also be made of substances represented by the following chemical formula I~III or their equivalents. Of course, potassium and lithium salts of the aforesaid substances may be used as well.

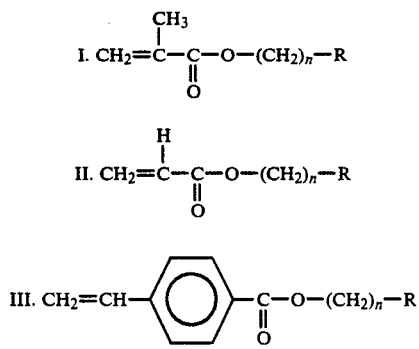

(R denotes 1 ~ 9 shown hereinbelow)

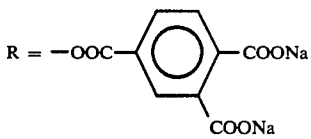

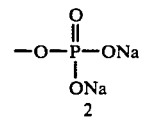

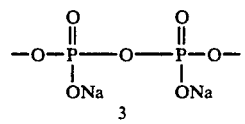

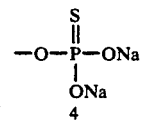

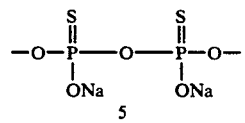

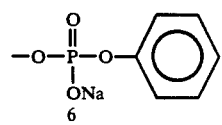

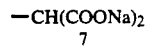

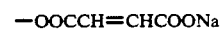

-continued

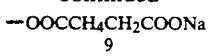

The substances used for liquid B in the form of a 1–70% aqueous solution may be one or more of chlorides, nitrates, sulfates and acetates of calcium, zinc, strontium, magnesium, aluminium, barium, iron, copper, silver, lead or tin, all being soluble in water. Part of water may be substituted by alcohol, acetone, dimethyl sulfoxide or the like. Specific mention is made of calcium chloride, zinc chloride, strontium chloride, magnesium chloride, aluminium chloride, iron chloride, copper chloride, barium nitrate, tin chloride, zinc sulfate, strontium sulfate, magnesium sulfate, aluminium sulfate, copper sulfate, calcium nitrate, zinc nitrate, strontium nitrate, magnesium nitrate, aluminium nitrate, iron nitrate, copper nitrate, silver nitrate, barium nitrate, lead nitrate, barium acetate, calcium acetate strontium acetate, magnesium acetate, zinc acetate and lead acetate and others.

Although not generally determinable, the substances may account for 1–70% of liquid A or B. However, the substances should preferably account for 3–30% of liquid A or B for the treatment of hypersensitivity and pulpalgia. At a concentration lower than 1%, the reaction product is less precipitated and applying should thus be repeated three or four times to seal up the root canal. At a concentration higher than 70%, on the other hand, it takes long to dissolve the component in water, rendering the work troublesome. A concentration range, which produces an effect in one operation, enables that effect to be maintained and makes dissolution work easy, is thus considered at 3–30%.

The substances should preferably account for 10–60% of a treating material of sealing up the root apex in the root canal. At a concentration lower than 10% the reaction product is so less precipitated that the root apex cannot be sealed up completely, while at a concentration higher than 60% it takes long to dissolve the component in water, rendering the work troublesome. A concentration range, which enables the root apex in the root canal to be sealed up in one operation and makes dissolution work easy, is thus considered to lie at 10–60%.

Liquids A and/or B may contain, in addition to water and the essential component, a monomeric component having one or more hydrophilic groups such as hydroxyl, carboxyl and sulfone groups and, at the same time, a polymerizable double bond. Illustrative mention, for instance, is made of 2-hydroxyethyl (meth)acrylate, 2-hydroxypropyl (meth)acrylate, 3-hydroxypropyl (meth)acrylate, 2,3-dihydroxypropyl (meth) acrylate, methacrylic acid, acrylic acid, 2-acrylamide-2-methylpropanesulfone acid, N-vinylpyrrolidone, polyethylene glycol di(meth)acrylate and their mixtures. Concentrations of these monomers in water are preferably in the range of 5–80%.

How to use the odontotherapeutical material according to this invention will now be explained.

For hypersensitivity:
(1) the affected region is cleaned and dried up;
(2) liquid A is applied on the affected region from a dental plate with a sponge;
(3) liquid B is applied on the coat of liquid A from another dental plate with a sponge; and
(4) excessive liquid deposited onto the affected and other parts is removed by a cotton pellet.

The order of application of liquids A and B may be reversed.

For treating pulpalgia (with a coating primer):
(1) A cavity cleaner commercialized by G-C Dental Industrial Corp. under the trade name of "GC Dentine Conditioner" is applied on the affected region to remove smear layers which have formed by the mechanical cutting of the dentin;
(2) the affected region is cleaned and dried up;
(3) liquid A is applied on the affected region with a sponge;
(4) liquid B is applied on the coat of liquid A with a sponge;
(5) excessive liquid deposited onto the affected and other parts is removed by a cotton pellet; and
(6) A dental bonding material is coated on the resulting coats for setting.

The order of application of liquids A and B may be reversed.

For sealing up the root apex in the root canal:
(1) The root canal is enlarged by a reamer, a file or the like, and the root canal is well cleaned inside;
(2) the root canal is again cleaned inside with Liquid A, using a dental syringe; and
(3) liquid B is forced through the root apex into the root canal, using a syringe again.

The order of application of liquids A and B may be reversed.

EXAMPLES

The odontotherapeutical materials according to this invention will now be explained more illustratively but not exclusively with reference to their examples. The components forming the odontotherapeutical materials are set out according to Examples 1–34.

EXAMPLE 1

A 5% aqueous solution of disodium phosphate was prepared as liquid A1, which was then adjusted to pH 7.4 with a 5% aqueous solution of monosodium phosphate.

Next, a 10% aqueous solution of calcium chloride was prepared as liquid B1, which was then adjusted to pH 7.4 with a 5% hydrochloric acid solution.

The affected region of a patient suffering from hypersensitivity was cleaned and dried, and liquid A1 were applied to it with the aid of a sponge. Subsequently, liquid B1 were applied to the coat of liquid A1 with the aid of a sponge. The pain was immediately removed from the patient.

EXAMPLES 2–22

The procedures of Example 1 were followed with the exception that liquids A2-22 and B2-22 were used. The results were the same as described in Example 1.

EXAMPLE 2

Liquid A2—A mixed liquid of a 5% aqueous solution of disodium phosphate with a 2% aqueous solution of sodium fluoride, which was adjusted to pH 7.2 with a 5% aqueous solution of monosodium phosphate.

Liquid B2—A 10% solution of calcium chloride, which was adjusted to pH 7.2 with a 5% aqueous solution of hydrochloric acid.

EXAMPLE 3

Liquid A3—A 10% aqueous solution of trisodium phosphate, which was adjusted to pH 7.0 with a 10% aqueous solution of monosodium phosphate.

Liquid B3—A 20% aqueous solution of zinc chloride, which was adjusted to pH 7.0 with a 5% aqueous solution of sodium hydroxide.

EXAMPLE 4

Liquid A4—A 10% aqueous solution of trisodium phosphate, which was adjusted to pH 7.0 with a 10% aqueous solution of monosodium phosphate.

Liquid B4—A 20 aqueous solution of strontium chloride, which was adjusted to pH 7.0 with a 1% aqueous solution of sodium hydroxide.

EXAMPLE 5

Liquid A5—A 5% aqueous solution of disodium phosphate, which was adjusted to pH 7.0 with a 55 aqueous solution of monosodium phosphate.

Liquid B5—A 20% aqueous solution of zinc chloride, which was adjusted to pH 7.0 with a 5% aqueous solution of sodium hydroxide.

EXAMPLE 6

Liquid A6—A 5% aqueous solution of disodium phosphate, which was adjusted to pH 7.0 with a 5% aqueous solution of monosodium phosphate.

Liquid B6—A 20% aqueous solution of strontium chloride, which was adjusted to pH 7.0 with a 5% aqueous solution of sodium hydroxide.

EXAMPLE 7

Liquid A7—A 5% aqueous solution of sodium pyrophosphate, which was adjusted to pH 7.4 with a 5% aqueous solution of monosodium phosphate.

Liquid B7—A 15% aqueous solution of calcium chloride, which was adjusted to pH 7.4 with a 5% aqueous solution of hydrochloric acid.

EXAMPLE 8

Liquid A—A 5% aqueous solution of sodium pyrophosphate, which was adjusted to pH 7.4 with a 5% aqueous solution of monosodium phosphate.

Liquid B8—A 10% aqueous solution of zinc chloride, which was adjusted to pH 7.4 with a 5% aqueous solution of sodium hydroxide.

EXAMPLE 9

Liquid A9—A 5% aqueous solution of sodium pyrophosphate, which was adjusted to pH 7.4 with a 5% aqueous solution of monosodium phosphate.

Liquid B9—A 20% aqueous solution of strontium chloride, which was adjusted to pH 7.4 with a 5% aqueous solution of sodium hydroxide.

EXAMPLE 10

Liquid A10—A 10% aqueous solution of sodium malonate, which was adjusted to pH 7.4 with a 5% aqueous solution of monosodium phosphate.

Liquid B10—A 10% aqueous solution of zinc chloride, which was adjusted to pH 7.4 with a 5% aqueous solution of sodium hydroxide.

EXAMPLE 11

Liquid A11—A 5% aqueous solution of sodium salicylate, which was adjusted to pH 7.4 with a 5% aqueous solution of monosodium phosphate.

Liquid B11—A 20% aqueous solution of zinc chloride, which was adjusted to pH 7.4 with a 5% aqueous solution of sodium hydroxide.

EXAMPLE 12

Liquid A12—A mixed liquid of a 5% aqueous solution of disodium phosphate with a 5% aqueous solution of sodium pyrophosphate, which was adjusted to pH 7.0 with a 5% aqueous solution of monosodium phosphate.

Liquid B12—A 20% aqueous solution of zinc chloride, which was adjusted to pH 7.0 with a 5% aqueous solution of sodium hydroxide.

EXAMPLE 13

Liquid A13—A mixed liquid of a 5% aqueous solution of disodium phosphate with a 5% aqueous solution of sodium polyacrylate, which was adjusted to pH 7.0 with a 5% aqueous solution of monosodium phosphate.

Liquid B13—A 20% aqueous solution of calcium chloride, which was adjusted to pH 7.0 with a 5% solution of hydrochloric acid.

EXAMPLE 14

Liquid A14—A mixed liquid of a 5% aqueous solution of disodium phosphate with a 5% aqueous solution of sodium polyacrylate, which was adjusted to pH 7.0 with a 5% aqueous solution of monosodium phosphate.

Liquid B14—A 20% aqueous solution of zinc chloride, which was adjusted to pH 7.0 with a 5% solution of sodium hydroxide.

EXAMPLE 15

Liquid A15—A mixed liquid of a 5% aqueous solution of disodium phosphate with a 1% aqueous solution of monosodium phosphate, which was adjusted to pH 7.0 with a 5% aqueous solution of monosodium phosphate.

Liquid B15—A 10% aqueous solution of calcium chloride, which was adjusted to pH 7.0 with a 5% solution of hydrochloric acid.

EXAMPLE 16

Liquid A16—A 2.5% aqueous solution of disodium phosphate, which was adjusted to pH 7.4 with a 2.5% aqueous solution of monosodium phosphate.

Liquid B16—A 5% aqueous solution of calcium chloride, which was adjusted to pH 7.4 with a 5% aqueous solution of hydrochloric acid.

EXAMPLE 17

Liquid 17—A 10% aqueous solution of disodium phosphate, which was adjusted to pH 7.4 with a 10% aqueous solution of monosodium phosphate.

Liquid B17—A 15% aqueous solution of calcium chloride, which was adjusted to pH 7.4 with a 5% aqueous solution of hydrochloric acid.

EXAMPLE 18

Liquid A18—A 2.5% aqueous solution of disodium phosphate, which was adjusted to pH 7.4 with a 5% aqueous solution of monopotassium phosphate.

Liquid B18—A 10% aqueous solution of calcium chloride, which was adjusted to pH 7.4 with a 5% aqueous solution of hydrochloric acid.

EXAMPLE 19

Liquid A19—A 2.5% aqueous solution of dipotassium phosphate, which was adjusted to pH 7.4 with a 2.5% aqueous solution of monosodium phosphate.

Liquid B19—A 5% aqueous solution of calcium chloride, which was adjusted to pH 7.4 with a 5% aqueous solution of hydrochloric acid.

EXAMPLE 20

Liquid A20—A 5% aqueous solution of dipotassium phosphate, which was adjusted to pH 7.4 with a 5% aqueous solution of monosodium phosphate.

Liquid B20—A 5% aqueous solution of calcium chloride, which was adjusted to pH 7.4 with a 5% aqueous solution of hydrochloric acid.

EXAMPLE 21

Liquid A21—A 10% aqueous solution of dipotassium phosphate, which was adjusted to pH 7.4 with a 10% aqueous solution of monosodium phosphate.

Liquid B21—A 5% aqueous solution of calcium chloride, which was adjusted to pH 7.4 with a 5% aqueous solution of hydrochloric acid.

EXAMPLE 22

Liquid A22—A 20% aqueous solution of dipotassium phosphate, which was adjusted to pH 7.4 with a 20% aqueous solution of monosodium phosphate.

Liquid B22—A 10aqueous solution of calcium chloride, which was adjusted to pH 7.4 with a 5% aqueous solution of hydrochloric acid.

EXAMPLE 23

A 5% aqueous solution of disodium phosphate was prepared as liquid A23, which was then adjusted to pH 7.4 with a 5% aqueous solution of monosodium phosphate.

Next, a 10% aqueous solution of calcium chloride was prepared as liquid B23.

The affected region of a patient suffering from hypersensitivity was cleaned and dried, and liquid A23 were applied to it with the aid of a sponge. Subsequently, liquid B23 were applied to the coat of Liquid B23 with the aid of a sponge. The pain was immediately removed from the patient.

EXAMPLE 24

A 5% aqueous solution of disodium phosphate was prepared as liquid A24.

Next, a 10% aqueous solution of calcium chloride was prepared as liquid B24.

The affected region of a patient suffering from hypersensitivity was cleaned and dried, and liquid A24 were applied to it with the aid of a sponge. Subsequently, liquid B24 were applied to the coat of liquid A24 from another dental plate with the aid of a sponge. The pain was immediately removed from the patient.

EXAMPLE 25

A 5% aqueous solution of disodium phosphate was prepared as liquid A25, which was then adjusted to pH 7.4 with a 5% aqueous solution of monosodium phosphate.

Then, 5% of calcium chloride was dissolved in an aqueous solution containing 25% of 2-hydroxyethyl methacrylate to form liquid B25, which was in turn adjusted to pH 7.4 with a 5% aqueous solution of hydrochloric acid.

For the filling of a dental resin, a Class I cavity was formed in the lower first molar of a patient. To remove smear layers, a cavity cleaner—commercialized by G-C Dental Industrial Corp. under the trade name of "Dentine Condition"—was applied on the cavity, followed by water cleaning and drying. Afterwards, liquid A25 was applied on the cavity with the aid of a sponge, and liquid B25 was then applied on the coat of liquid A25 with the aid of a sponge. The resulting coats were allowed to stand for about 30 seconds. Air was subsequently blown into the cavity with a dental syringe for drying the coats, followed by the application of a light cured composition consisting of 30% of 2-hydroxyethyl methacrylate, 68% of triethylene glycol dimethacrylate, 1% of dimethylaminoethyl methacrylate and 1% of camphor-quinone. The resulting coats were exposed to visible light with a dental visible light irradiator for one minute for setting. Afterwards, a light cured type of a resin—commercialized by G-C Dental Industrial Corp. under the trade name of "Graft LC"—was filled in the cavity and set by a 30-second irradiation of visible light with a dental visible light irradiator. The patient was substantially released from pain and kept in good condition even after the lapse of one month.

EXAMPLES 26 & 27

The procedures of Example 25 were followed with the exception that liquids A26-27 and B26-27, mentioned just below, were used. The results were the same as described in Example 25.

Liquid A26—A 5% aqueous solution of disodium phosphate, which was adjusted to pH 7.4 with a 5% aqueous solution of monosodium phosphate.

Liquid B26—10% of zin oxide was dissolved in an aqueous solution containing 30% of 2-hydroxyethyl methacrylate oxide, which was adjusted to pH 7.4 with a 5% aqueous solution of sodium hydroxide.

Liquid A27—A mixed liquid of a 5% aqueous solution of disodium phosphate with a 1% aqueous solution of sodium vinyl benzoate, which was adjusted to pH 7.4 with a 5% aqueous solution of monosodium phosphate.

Liquid B27—10% of calcium chloride was dissolved in an aqueous solution containing 20% of 2-hydroxyethyl methacrylate, which was adjusted to pH 7.4 with a 5% aqueous solution of hydrochloric acid.

EXAMPLE 28

A 5% aqueous solution of disodium phosphate was prepared as liquid A28, which was then adjusted to pH 7.4 with a 5% aqueous solution of monosodium phosphate.

Then, a 10% aqueous solution of calcium chloride was prepared as liquid B28, which was in turn adjusted to pH 7.4 with a 5% aqueous solution of hydrochloric acid.

For the filling of a dental resin, a Class I cavity was formed in the upper first molar of a patient. To remove smear layers, a cavity cleaner—commercialized by G-C Dental Industrial Corp. under the trade name of "Dentine Conditioner"—was applied on the cavity, followed by water washing and drying. Afterwards, liquid A28 was coated on the cavity with the aid of a sponge, and liquid B26 was then applied on the coat of liquid A28 with the aid of a sponge. The resulting coats were allowed to stand for about one minute. Air was subsequently blown onto the cavity with a dental syringe for drying the coats, followed by the application of a light cured composition—commercialized by Kuraray Co., Ltd. under the trade name of "Photobond". The resulting coats were exposed to visible light with a dental visible light irradiator for one minute for setting. Afterwards, a light cured type of resin—commercialized by Kuraray Co., Ltd. under the trade name of "Photo-Clearfil"—was filled in the cavity and set by a 60-second irradiation of visible light with a dental visible light irradiator. The patient was substantially released from pain and kept in good condition even after the lapse of two months.

EXAMPLE 29

A 5% aqueous solution of disodium phosphate was mixed with 1% of sodium vinyl benzoate to prepare liquid A29, which was then adjusted to pH 7.4 with a 5% aqueous solution of monosodium phosphate.

Then, a 10% aqueous solution of calcium chloride was prepared as liquid B29, which was in turn adjusted to pH 7.4 with a 5% aqueous solution of hydrochloric acid.

For the filling of a dental resin, a Class I cavity was formed in the upper first molar of a patient. To remove smear layers, a cavity cleaner—commercialized by G-C Dental Industrial Corp. under the trade name of "Dentine Conditioner"—was coated on the cavity, followed by water cleaning and drying. Afterwards, liquid A29 was coated on the cavity with the aid of a sponge, and liquid B29 was then coated on the coat of liquid A29 with the aid of a sponge. The resulting coats were allowed to stand for about 30 seconds. Air was subsequently blown onto the cavity with a dental syringe for drying the coats, followed by the application of a light cured composition—commercialized by Kuraray Co., Ltd. under the trade name of "PhotoBond". The resulting coats were exposed to visible light with a dental visible light irradiator for 30 seconds for setting. Afterwards, a light cured type of resin—commercialized by Kuraray Co., Ltd. under the trade name of "Photo-Clearfil"—was filled in the cavity and set by a 60-second irradiation of visible light with a dental visible light irradiator. The patient was substantially released from pain and kept in good condition even after the lapse of three months.

EXAMPLE 30

The procedures of Example 29 were followed with the exception that a 5% aqueous solution of disodium phosphate adjusted to pH 7.4 with a 5% aqueous solution of monosodium phosphate was used as liquid A30; a 30% aqueous solution of 2-hydroxyethyl methacrylate in which 5% of calcium chloride was dissolved and which was adjusted to pH 7.4 with a 5% aqueous solution of hydrochloric acid was employed as liquid B30; and coats were exposed to visible light for one minute. The results were the same as mentioned in Example 29.

EXAMPLE 31

A 5% aqueous solution of disodium phosphate was prepared as liquid A31, which was then adjusted to pH 7.4 with a 5% aqueous solution of monosodium phosphate.

Then, a 10% aqueous solution of calcium chloride was prepared as liquid B31, which was in turn adjusted to pH 7.4 with a 5% aqueous solution of hydrochloric acid.

For the filling of a dental resin, a Class I cavity was formed in the lower second premolar of a patient. To remove smear layers, a cavity cleaner—commercialized by G-C Dental Industrial Corp. under the trade name of "Dentine Conditioner"—was coated on the cavity, followed by water cleaning and drying. Afterwards, liquid A31 was coated on the cavity with the aid of a sponge, and liquid B31 was then coated on the coat of liquid A31 with the aid of a sponge. The resulting coats were allowed to stand for about 30 seconds. Air was subsequently blown onto the cavity with a dental syringe for drying the coats, followed by the filling and setting of a light cured type of resin—commercialized by ICI Co., Ltd. under the trade name of "Occlusin". The patient was substantially released from pain and kept in good condition even after the lapse of one month.

EXAMPLE 32

The procedures of Example 31 were followed with the exception that a mixture of a 3% aqueous solution of disodium phosphate with a 6% aqueous solution of sodium vinyl benzoate, which was adjusted to pH 7.4 with a 5% aqueous solution of monosodium phosphate, was used as liquid A32; and a 10% aqueous solution of calcium chloride adjusted to pH 7.4 with a 5% aqueous solution of hydrochloric acid was employed as liquid B32. The results, even after the lapse of 2 months, were the same as mentioned in Example 31.

EXAMPLE 33

A 5% aqueous solution of disodium phosphate was prepared as liquid A33, which was then adjusted to pH 7.4 with a 5% aqueous solution of monosodium phosphate. Then, a 10% aqueous solution of zinc chloride was prepared as liquid B33, which was in turn regulated to pH 7.4 with a 5% aqueous solution of sodium hydroxide.

For the filling of a dental resin, a Class I cavity was formed in the lower second premolar of a patient. To remove smear layers, a cavity cleaner—commercialized by G-C Dental Industrial Corp. under the trade name of "GC Dentine Conditioner"—was coated on the cavity, followed by water cleaning and drying. Afterwards, liquid A33 was coated on the cavity with the aid of a sponge, and liquid B33 was then coated on the coat of liquid A33 with the aid of a sponge. The resulting coats were allowed to stand for about 30 seconds. Air was subsequently blown onto the cavity with a dental syringe for drying the coats, followed by the application of a light cured composition consisting of 30% of 2-hydroxyethyl methacrylate, 68% of triethylene glycol dimethacrylate, 1% of dimethylaminoethyl methacrylate and 1% of camphor-quinone. The resulting coats were exposed to visible light with a dental visible light irradiator for one minute for setting. Afterwards, a light cured type of a resin—commercialized by G-C Dental Industrial Corp. under the trade name of "GC Graft LC"—was filled in the cavity and set by a 30-second irradiation of visible light with a dental visible light irradiator. The patient was substantially released from pain and kept in good condition even after the lapse of three months.

EXAMPLE 34

A 5% aqueous solution of disodium phosphate was prepared as Liquid A34, which was then adjusted to pH 7.4 with a 5% aqueous solution of monosodium phosphate. Then, a 10% aqueous solution of calcium chloride was prepared as liquid B34, which was in turn adjusted to pH 7.4 with a 5% aqueous solution of hydrochloric acid.

After tooth preparation for fixed prosthodontics with a diamond point, the affected region of a patient suffering from pain was cleared and dried up. Liquid A34 was applied on the affected region with the aid of a sponge, and liquid B34 was coated on the coat of liquid A34 with the aid of a sponge. The patient was immediately released from the pain.

EXAMPLE 35

A 5% aqueous solution of disodium phosphate was mixed with a 2% aqueous solution of sodium fluoride to prepare liquid A35, which was in turn adjusted to pH 7.2 with a 5% aqueous solution of monosodium phosphate. Then, a 10% aqueous solution of calcium chloride was prepared as liquid B35, which was in turn adjusted to pH 7.2 with a 5% aqueous solution of hydrochloric acid.

As the affected region of a patient suffering from furcation involvement was subjected to root planning, the patient complained of a pain. After cleaning and drying up the affected region, liquid A35 was applied on that region with the use of a sponge, and liquid B35 was coated on the coat of liquid A35 with a sponge. The patient was immediately relieved of the pain.

EXAMPLE 36

A 10% aqueous solution of disodium phosphate was prepared as liquid A36, which was in turn adjusted to pH 7.4 with a 5% aqueous solution of monosodium phosphate. Then, a 15% aqueous solution of calcium chloride was prepared as liquid B36, which was in turn adjusted to pH 7.4 with a 5% aqueous solution of hydrochloric acid.

After the molar required to receive a root canal treatment was reamed and filed to enlarge the root canal and the root canal was fully cleaned inside, it was again cleaned inside with liquid A36, using a dental syringe. Then, liquid B36 was forced near the apical foramen into the root canal, using again a dental syringe for obtaining precipitates. Some paper points were then used to remove excessive liquid, followed by inspection with roentgen equipment. After it was confirmed that the apical foramen was sealed up, some gutta-percha points were filled in the root canal. After six months, roentgenograpy confirmed that the periradicular and periodontal tissues were kept in good condition.

COMPARATIVE EXAMPLE 1

A diammine silver fluoride preparation containing a diammine silver fluoride solution—commercialized by Bibrand Medico Dental Co., Ltd. under the trade name of "Saforide"—was applied to a patient complaining of hypersensitivity, bu the patient was not relieved of the pain. The patient's teeth became black.

COMPARATIVE EXAMPLE 2

The patient was exposed for 30 seconds to soft laser with "Stmalaser" made by Sedatelec Co., Ltd. However, the pain was removed from the upper jaw, but the lower jaw was still in an ill condition.

COMPARATIVE EXAMPLE 3

For the filling of a dental resin, a Class II cavity was formed in the upper first molar of a patient. Applied on the cavity, a light cured composition—commercialized by Kuraray Co., Ltd. under the trade name of "Photo-Bond"—was set by a one-minute exposure to visible light with a dental visible light irradiator. Afterwards, a light cured type of a resin—commecialized by Kuraray Co., Ltd. under the trade name of "PhotoClearfil'-'—was filled in the cavity, followed by a 30-second exposure to visible light with a dental visible light irradiator. Immediately after the filling, the patient complained of a pain. The pain lingered for one week. On the 10th day on which the pain became more serious, pulpectomy was performed.

COMPARATIVE EXAMPLE 4

The molar required to receive a root canal treatment was reamed and filed to enlarge the root canal and the root canal was well-cleaned inside. Afterwards, some paper points were used to remove excessive water and some gutta-percha points were then filled in the root canal.

After the filling, roentgenography indicated that the point thrusted about 1 mm through the root apex. On the next day, the inflammation became more serious and the pain increased. Thus, the root canal treatment had to be performed again.

According to this invention, liquids A and B containing substances capable of form difficult-to-dissolve precipitates rapidly by mixing are successively applied on the affected region, on which they are permitted to react with each other to form the difficult-to-dissolve substance, thereby sealing up an elongated dentinal tubule.

Liquid A is mainly an aqueous solution containing 1–70% of one or more of sodium, potassium and lithium salts of inorganic or organic acids, while liquid B is chiefly an aqueous solution containing 1–70% of one or more of chlorides, nitrates, sulfates and acetates of calcium, zinc, strontium, magnesium, aluminium, barium, iron, copper, silver, lead or tin.

When the odontotherapeutical material according to this invention is used as a lenitive for hypersensitivity, liquid A is applied on the affected region, already cleaned and dried up, with a sponge, and liquid B is then coated on the coat of liquid A with a sponge. The order of application of liquids A and B may be reversed.

When the odontotherapeutical material according to this invention is used as a pulpalgia lenitive (or a coating primer), a cavity cleaner commercialized by G-C Dental Industrial Corp. under the trade name of "GC Dentine Conditioner" is applied to the dentinal part of the affected region to remove smear layers, followed by the cleaning and drying of the affected region. Liquid A is applied on the affected region with a sponge, and liquid B is coated on the coat of liquid A with a sponge. Afterward, a dental bonding material is applied on the resulting coats for setting. The order of application of liquids A and B may be reversed.

When the odontotherapeutical material according to this invention is used to seal up the root apex in the root canal, the root canal is enlarged by a reamer, a file, etc. and is then well cleaned inside. Afterwards, the root canal is again cleaned inside with liquid A, using a dental syringe. Subsequently, liquid B is forced through the root apex into the root canal, using again a syringe. The order of application of liquids A and B may be reversed.

As detailed above, when the odontotherapeutical material according to this invention is used as the lenitive for hypersensitivity, liquids A and B with or without adjusted pH are successively applied on the affected region for the reaction of them with each other, forming a difficult-to-dissolve substance capable of sealing up elongated dentinal tubules. This makes it possible to control such a fluid movement in dentinal tubules as referred to in the Brënnströom's hydrodynamic theory, cutting off stimuli to the dental pulp.

The odontotherapeutical material according to this invention can also meet all the eight items of requirements, enumerated below, which the conventional lenitive for hypersensitivity is supposed to possess:

(1) it should be unstimulating to the dental pulp and gingival and mitigate or remove an induced pain;
(2) it should cause no damage to teeth;
(3) it should cause no discoloration of teeth;
(4) it should produce its effect through simple work;
(5) it should achieve its effect immediately;
(6) it should sustain its effect;
(7) it should cause no pain to the patient during or after treatment; and
(8) it should dispense with special hardware or equipment.

When the odontotherapeutical material according to this invention is used as the pulpalgia lenitive (a coating primer), liquids A and B with or without adjusted pH are successively applied on the affected region, on which they are reacted with each other to form a difficult-to-dissolve substance in the dentinal tubules and on the dentinal surface, which may then be set with or without a light cured composition. This renders it possible to control such a fluid movement in tubules as referred to in the Brännström's hydrodynamic theory, cutting of stimuli to the dental pulp. The odontotherapeutical material according to this invention also enables commercially available dental cements or liners used as bases to be filled in place and dental resins to be placed thereon with greater safety. Taken altogether, the odontotherapeutical material according to this invention can meet all the nine items of requirements, enumerated below, which the conventional pulpalgia lenitive is supposed to possess:

(1) it should be unstimulating to the dental pulp and gingival and mitigate or remove an induced pain;
(2) it should cause no damage to dentin;
(3) it should cause no discoloration of dentin;
(4) it should produce its effect through simple work;
(5) it should achieve its effect immediately;
(6) it should sustain its effect;
(7) it should cause no pain to the patient during or after treatment;
(8) it should dispense with special hardware or equipment; and
(9) it should take no part in the polymerization of resin.

Also, the odontotherapeutical material according to this invention can be used after scaling or root planing.

Also, the odontotherapeutical material according to this invention can be used to learn whether the pain is induced by hypersensitivity or pulpitis.

Further, when the odontotherapeutical material according to this invention is used to seal up the apex in the root canal, liquids A and B with or without adjusted pH are successively forced into the root canal, in which they are reacted with each other to form a difficult-to-dissolve substance and thereby seal up the root apex stationarily. Thus, the thrusting of a gutta-percha point through the root apex, which is one of the problems with the conventional material, can be avoided.

What is claimed is:

1. An odontotherapeutical material comprising two liquids A and B containing materials which form difficult-to-dissolve precipitations when said liquids A and B are mixed, said liquid A comprising an aqueous solution of 10–70% of at least one compound selected from the group consisting of sodium phosphate, potassium phosphate, sodium fluoride, sodium pyrophosphate, sodium acrylate, and mixtures thereof, and said liquid B comprising an aqueous solution of 10–70% of strontium chloride.

2. An odontotherapeutical material comprising two liquids A and B containing materials which form difficult-to-dissolve precipitations when said liquids A and B are mixed, said liquid A comprising an aqueous solution of 1–70% of at least one first compound selected from the group consisting of sodium phosphate, potassium phosphate, sodium fluoride, sodium pyrophosphate, sodium acrylate, and mixtures thereof, and said liquid B comprising an aqueous solution of 15–70% of at least one second compound selected from the group consisting of calcium chloride, zinc chloride, strontium chloride and mixtures thereof.

3. The odontotherapeutical material of claim 1 or 2, further comprising a photocurable polymer.

4. The odontotherapeutical material of claim 1 or 2, wherein the percentage of said first compound in said liquid A is 10–60% and the percentage of said second compound in said liquid B is 10–60%.

5. The odontotherapeutical material of claim 2, wherein said second compound in said liquid B is selected from the group consisting of zinc chloride, strontium chloride and mixtures thereof.

6. The odontotherapeutical material of claim 2, wherein said second compound in said liquid B is calcium chloride, present in a percentage of 15–70%.

7. The odontotherapeutical material of claim 6, wherein said calcium chloride is present in a percentage of 15–60%.

8. The odontotherapeutical material of claim 6, wherein said calcium chloride is present in a percentage of 15–20%.

9. An odontotherapeutical material as claimed in claim 1 or 2, wherein the liquids A and/or B contain in addition to water and the essential components, a monomeric material containing one or more hydrophilic groups such as hydroxyl, carboxyl and sulfone groups and, at the same time, a polymerizable double bond.

10. An odontotherapeutical material as claimed in claim 1 or 2, wherein the liquids A and/or B contain, in addition to water and the essential components, 1–70% of 2-hydroxyethyl methacrylate.

* * * * *